(12) United States Patent
Dorsett et al.

(10) Patent No.: US 9,138,424 B2
(45) Date of Patent: Sep. 22, 2015

(54) METHODS AND COMPOSITIONS FOR TREATING CORNELIA DE LANGE SYNDROME

(71) Applicant: Saint Louis University, St. Louis, MO (US)

(72) Inventors: Dale Dorsett, St. Louis, MO (US); Justin Fay, St. Louis, MO (US)

(73) Assignees: Saint Louis University, St. Louis, MO (US); Washington University, St. Louis, MO (US)

( * ) Notice: Subject to any disclaimer, the term of this patent is extended or adjusted under 35 U.S.C. 154(b) by 231 days.

(21) Appl. No.: 13/889,314

(22) Filed: May 7, 2013

(65) Prior Publication Data
US 2013/0303584 A1   Nov. 14, 2013

Related U.S. Application Data

(60) Provisional application No. 61/646,191, filed on May 11, 2012.

(51) Int. Cl.
*A61K 31/405* (2006.01)

(52) U.S. Cl.
CPC .................................. *A61K 31/405* (2013.01)

(58) Field of Classification Search
None
See application file for complete search history.

*Primary Examiner* — Savitha Rao
*Assistant Examiner* — Gregg Polansky
(74) *Attorney, Agent, or Firm* — Randolph Bretton; The Law Office of Randolph Bretton

(57) ABSTRACT

Disclosed are methods and compositions for treating subjects with Cornelia de Lange Syndrome (CdLS). Specifically disclosed are methods for using Indomethacin or Acemetacin to treat subjects with CdLS. Also disclosed are methods for identifying compounds beneficial for the treatment of CdLS using an assay based on the expression of NIPBL or NIPBL homologous or orthologous genes. Also disclosed is a method of identifying compounds beneficial for the treatment of CdLS based on administering a test compound to *Drosophila* lava with reduced expression of Nipbl, and determining the normalization of CdLS phenotypes.

20 Claims, 8 Drawing Sheets

SEQUENCE LISTING

```
<160> NUMBER OF SEQ ID NOS: 12

<210> SEQ ID NO 1
<211> LENGTH: 23
<212> TYPE: DNA
<213> ORGANISM: Homo sapiens

<400> SEQUENCE: 1
aaagcacacc ctgacaataa ggc                                               23

<210> SEQ ID NO 2
<211> LENGTH: 23
<212> TYPE: DNA
<213> ORGANISM: Homo sapiens

<400> SEQUENCE: 2
tccctcttga ttttcggaat gac                                               23

<210> SEQ ID NO 3
<211> LENGTH: 21
<212> TYPE: DNA
<213> ORGANISM: Homo sapiens
```

```
<400> SEQUENCE: 3
caagaaggtg gtgaagcagg c                                              21

<210> SEQ ID NO 4
<211> LENGTH: 23
<212> TYPE: DNA
<213> ORGANISM: Homo sapiens

<400> SEQUENCE: 4
cgctgttgaa gtcagaggag acc                                            23

<210> SEQ ID NO 5
<211> LENGTH: 23
<212> TYPE: DNA
<213> ORGANISM: Mus musculus

<400> SEQUENCE: 5
tgaaacccca aagcaaaaga gtg                                            23

<210> SEQ ID NO 6
<211> LENGTH: 22
<212> TYPE: DNA
<213> ORGANISM: Mus musculus

<400> SEQUENCE: 6
agtctcaggt cgtccatcac cc                                             22

<210> SEQ ID NO 7
<211> LENGTH: 23
<212> TYPE: DNA
<213> ORGANISM: Mus musculus

<400> SEQUENCE: 7
gcaaggacac tgagcaagag agg                                            23

<210> SEQ ID NO 8
<211> LENGTH: 22
<212> TYPE: DNA
<213> ORGANISM: Mus musculus

<400> SEQUENCE: 8
ttattatggg ggtctgggat gg                                             22

<210> SEQ ID NO 9
<211> LENGTH: 21
<212> TYPE: DNA
<213> ORGANISM: Drosophila melanogaster

<400> SEQUENCE: 9
aggttatgcg agtcgtggac c                                              21

<210> SEQ ID NO 10
<211> LENGTH: 24
<212> TYPE: DNA
<213> ORGANISM: Drosophila melanogaster

<400> SEQUENCE: 10
gcggtttagt agtgcgaaga agtg                                           24

<210> SEQ ID NO 11
<211> LENGTH: 22
<212> TYPE: DNA
```

```
<213> ORGANISM: Drosophila melanogaster

<400> SEQUENCE: 11
atcggttacg gatcgaacaa gc                                              22

<210> SEQ ID NO 12
<211> LENGTH: 22
<212> TYPE: DNA
<213> ORGANISM: Drosophila melanogaster

<400> SEQUENCE: 12
gttctgcatg agcaggacct cc                                              22
```

METHODS AND COMPOSITIONS FOR TREATING CORNELIA DE LANGE SYNDROME

CROSS REFERENCE TO RELATED APPLICATIONS

This application claims priority to provisional application 61/646,191, filed May 11, 2012, which is hereby incorporated by reference in its entirety.

GOVERNMENT FUNDING

This work was supported by National Institutes of Health grant no. 3R01GM055683-10A2S1. The government of the United States may have certain rights in this invention.

FIELD OF THE INVENTION

The invention relates to methods and compositions, for treating Cornelia de Lange Syndrome, and also methods of screening potential therapeutic agents for treating Cornelia de Lange Syndrome.

BACKGROUND

Cornelia de Lange Syndrome (CdLS) is a devastating genetic syndrome that occurs approximately once per 10,000 births and displays slow growth, physical deformities in limbs, heart and kidney, mental retardation, speech deficits and autism (Dorsett and Krantz (2009) Ann NY Acad. Sci. 1151:22-37). It is rarely inherited, and usually caused by sporadic dominant mutations. CdLS is associated with poor growth and diverse physical deformities and mental deficits. CdLS displays many features commonly seen in isolation in sporadic birth defects, and thus treatments developed for CdLS may also be beneficial for developmental disorders of unknown etiology. CdLS birth defects include clinically diagnostic facial features, upper limb deformities, and gut, heart, and kidney abnormalities. Other deficits include mental retardation (average IQ in the 50's), speech difficulties, and autism. CdLS has a significant lifestyle and financial impact on families, as CdLS individuals often require fulltime care for their entire life.

CdLS is caused by mutations in genes that encode proteins that mediate sister chromatid cohesion and control gene expression (Dorsett and Krantz 2009 Ann N Y Acad. Sci. 1151:22-37). Over half the cases are caused by dominant loss-of-function mutations in NIPBL, the human ortholog of the Nipped-B Drosophila gene. Some 5% are caused by dominant mild missense mutations in SMC1A. SMC1A is a subunit of the cohesin protein complex that holds sister chromatids together until a cell divides, and NIPBL loads cohesin onto chromosomes. Changes in gene expression are the likely source of the CdLS birth defects. In model organisms and CdLS cells, many genes important for growth and development are dysregulated. The Inventors reasoned that if CdLS can be diagnosed early, preferably upon birth, or prenatally, a drug therapy based on early intervention may ameliorate some postnatal growth and developmental deficits. The reduction in NIPBL expression in CdLS is 30% or less, and thus a modest increase in NIPBL function will likely be beneficial. Moreover, treating the source deficit would be more effective than trying to treat the many downstream consequences. Current evidence suggests that brain development is particularly plastic, and thus it may be possible to treat older individuals. Cognitive function is the most critical for self-care, and treatments than can improve these functions will reduce the impact on CdLS families.

There are currently no treatments for CdLS that address the root cause of the syndrome and improve physical growth and mental development. These are the critical phenotypes that greatly impact the ability of individuals with CdLS to function normally, and the abilities of their families to care for them over many years. Using yeast, Drosophila, and mouse cells, the Inventors have discovered a rapid, cost-effective method for screening potential therapeutic compounds for the treatment of CdLS, and have also identified specific compounds, useful for the treatment of CdLS.

SUMMARY OF THE INVENTION

A method of treating Cornelia de Lange Syndrome (CdLS) in a subject by administering an effective amount of Indomethacin or Acemetacin wherein the cellular expression levels of NIPBL or NIPBL homologous or orthologous mRNA are increased.

A method of identifying compounds beneficial for the treatment of Cornelia de Lange Syndrome by administering a test compound to a eukaryotic cell and measuring expression of NIPBL or NIPBL homologous or orthologous genes, wherein the expression of the NIPBL or the homologous or orthologous genes are increased.

A method of identifying compounds beneficial for the treatment of Cornelia de Lange Syndrome by administering a test compound to Drosophila larvae with reduced expression of Nipped-B, and determining the normalization of Nipped-B phenotypes.

DETAILED DESCRIPTION OF THE INVENTION

Figure 1:
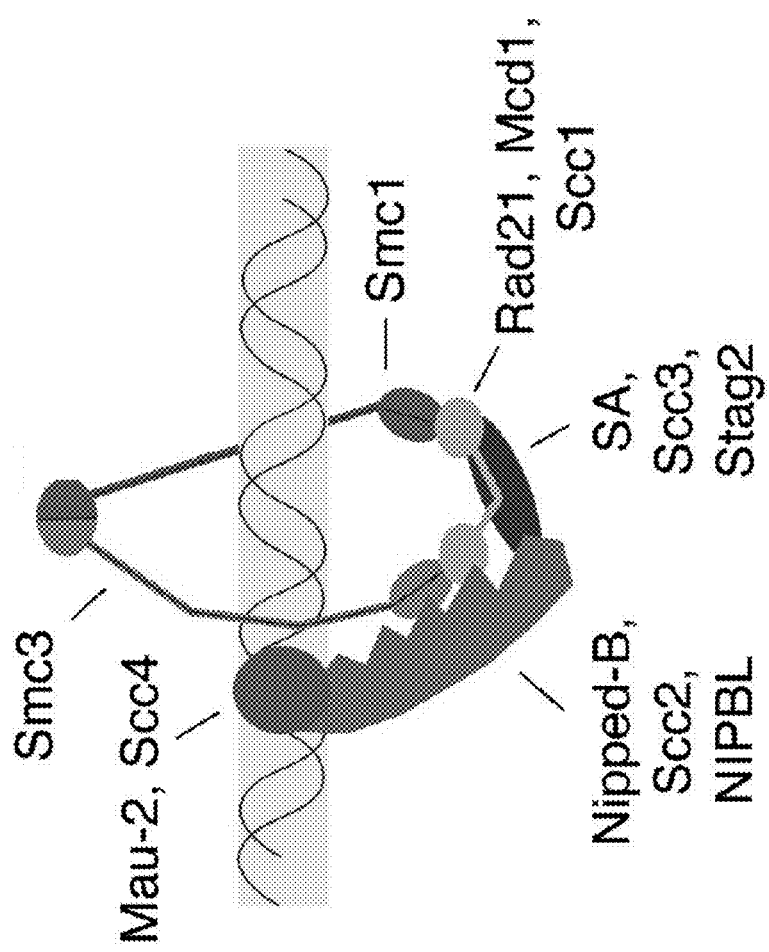
FIG. 1 illustrates the molecular relationship between NIPBL or Nipped-B and the cohesin complex and its subunits.

More than half of all CdLS are caused by heterozygous loss-of-function mutations in a developmental gene designated NIPBL (Krantz et al., (2004) Nat Genet.; 36(6):631-5; Tonkin et al., (2004) Nat Genet.; 36(6):636-414; Dorsett and Krantz (2009) Ann N Y Acad. Sci. 1151:22-37). NIPBL encodes a protein which interacts with a protein complex designated cohesin. NIPBL and the cohesin protein complex are required for sister chromatid cohesion, which ensures that chromosomes segregate properly upon cell division. The NIPBL gene is homologous and orthologous to the Nipped-B developmental gene in *Drosophila*, which has been extensively studied. Cohesin comprises a large ring-like structure that topologically encircles DNA, and NIPBL loads cohesin onto chromosomes (see FIG. 1). Cohesin subunits have been designated Smc1 (SMC1A), Smc3, Rad21 and SA (STAG2). CdLS is more rarely caused by mild open-frame-conserving mutations in the SMC1A and SMC3 genes encoding subunits of the cohesin complex.

The first evidence that NIPBL, or its homologs or orthologs, regulate gene expression and development was recovery of heterozygous loss-of-function *Drosophila* Nipped-B mutations in genetic screens for factors that regulate the cut and Ultrabithorax developmental genes in *Drosophila* in the Inventor's laboratory (Rollins et al., (1999) Genetics, 152(2):577-93; Rollins et al., (2004) Mol. Cell Biol., 24(8):3100-11). This work also showed that Nipped-B expression is only reduced by 25% in a heterozygous null mutant, indicating an unusual dosage compensation, but similar to that seen for NIPBL mutations in humans and mice (Kawauchi et al., (2009) PLoS Genet.; 5(9):e1000650; Liu et al., (2009) PLoS Biol. 5; 7(5):e1000119). Reduction to 50% by in vivo RNA interference (RNAi) in *Drosophila* has been seen to be lethal in the Inventor's laboratory (Rollins et al., (2004) Mol. Cell Biol.; 24(8):3100-11). Subsequent genome-wide studies by the Inventors revealed that Nipped-B and cohesin selectively bind approximately 30% of active genes that are enriched for those that control growth and development. Cohesin activates expression of many genes and represses others. Similar gene subsets are dysregulated in *Drosophila* brain. Subsequent studies in the Krantz and Musio laboratories revealed that some 5% of CdLS cases are caused by dominant mild missense mutations in SMC1A, which encodes a cohesin subunit (Musio et al., (2006) Nat Genet.; 38(5):528-30; Deardorff et al., (2007) Am J Hum Genet., 80(3):485-94). One CdLS individual has been found with a heterozygous missense SMC3 mutation. A few CdLS individuals have mutations in HDAC8, which encodes an enzyme that recycles the cohesin complex, and other individuals with CdLS-like features have mutations affecting the RAD21 cohesin subunit (Deardorff et al., (2012) Nature 489 (7415):313-7; Deardorff et al., (2012) Am J Hum Genet 90(6):1014-27). The cohesin subunit mutations in general cause a milder form of CdLS, with fewer physical abnormalities, but significant mental retardation.

The Inventors discovered that partial loss of function of cohesin or its subunits in *Drosophila melanogaster*, alters the expression of other genes and causes a number of developmental consequences (Rollins et al., (1999) Genetics 152(2): 577-93; Rollins et al., (2004) Mol. Cell Biol. 24(8):3100-11; Dorsett et al., (2005) Development; 132(21):4743-53; Seitan et al., (2006) PLoS Biol. 4(8):e242; Gause et al., (2008) Chromosoma 117(1):51-66; Schaaf et al. (2009) PLoS One, 4(7):e6202; Fay et al. (2011) Curr. Biol. 21(19):1624-34; Schaaf et al., (2013a) PLoS Genet 9(3):e1003382; Schaaf et al., (2013b) PLoS Genet, in press). Human mutations in NIPBL are very similar to those found in Nipped-B (Gause et al., (2008) Chromosoma 117(1):51-66; Gillis et al., (2004) Am J Hum Genet., 75(4):610-23). These mutations are also similar to *Drosophila* Nipped-B mutations in that heterozygous NIPBL alleles only reduce expression of NIPBL by 30% or less instead of the expected 50% (Liu et al., (2009) PLoS Biol. 5; 7(5):e1000119). This unusual dosage compensation is observed in Nipped-B in *Drosophila* (Rollins et al. (2004) Mol. Cell Biol., 24(8):3100-11), indicating another level of conservation between mutation and expression with *Drosophila* and humans. Significant defects in chromosome segregation in NIPBL mutant cells have not been observed, but there is a conserved pattern of gene dysregulation (Kaur et al., (2005) Am J Med Genet A.; 138 (1): 27-31; Liu et al. (2009) PLoS Biol. 5; 7(5):e1000119; Vrouwe et al., (2007) Hum Mol Genet.; 16(12):1478-87). Genome-wide mapping of NIPBL and cohesin chromosome binding in human lymphocytes revealed a similar pattern to that seen in *Drosophila*, in that binding is highest around the transcription start sites of active genes (Misulovin et al., (2008) Chromosoma.; 117(1): 89-102; Liu et al., (2009) PLoS Biol., 5; 7(5):e1000119). Also, lymphocytes and fibroblasts derived from CdLS individuals with different NIPBL mutations have a characteristic pattern of gene dysregulation. Id.

The Inventors reasoned that the broad spectrum of developmental deficits in CdLS may be treated with a therapy that targets the source deficit in NIPBL or cohesin expression or function, which has drastic consequences downstream. This may be accomplished by administration of a compound that increases the cellular expression or activity of the NIPBL gene.

In addition, defects characteristic of CdLS can also be seen in mice with altered Nipbl genes (Kawauchi et al. (2009) PLoS Genet.; 5(9):e1000650). Heterozygous Nipbl mice display many developmental deficits characteristic of CdLS, including poor growth, reduced adipogenesis, heart defects (which kill about 75% of the Nipbl −/+ mice), hearing deficits, and repetitive behaviors. Similar to human and *Drosophila*, Nipbl expression is only reduced by 30% in these mice, indicating another level of conservation between mice, *Drosophila*, and human cells. The NIPBL protein is also found to have homologues and orthologs in yeast, known as Scc2p, and Mis4p. These are essential proteins, but yeast with temperature-sensitive mutations in these proteins are viable with reduced growth rates at semi-permissive temperatures.

Based on the conservation of human NIPBL homologs and orthologs in *Drosophila* (Nipped-B), mice (Nipbl,) and yeast (Scc2p, Mis4p), the Inventors reasoned that cells derived from *Drosophila*, mouse, human, or yeast, deficient in the expression NIPBL, or its homologs and orthologs, may be used to screen potential therapeutic compounds for the ability to increase NIPBL expression at the cellular level, and improve developmental events downstream which are believed to be responsible for at least some symptoms observed in subjects with CdLS. Furthermore, the Inventors reasoned that *Drosophila*, deficient in Nipped-B expression, may be treated with potential therapeutic compounds during the developmental stages of their life cycle, and used to screen these compounds for the ability to normalize or improve this developmental phenotype and provide therapeutic benefits for subjects with CdLS.

The Inventors first conducted screens for therapeutic compounds that improve the growth of yeast scc2 and mis4 mutants (Example 1). Compounds that improved the growth of mutant yeast were then tested for their ability to modify Nipped-B-dependent mutant developmental phenotypes in *Drosophila*. This was done by feeding Acemetacin and Indomethacin to *Drosophila* larvae from the time of hatching until pupariation (Example 2). These compounds were also tested for their ability to increase expression of Nipped-B and Nipped-B-dependent genes in cultured *Drosophila* cells (Example 2), as well as their ability to increase expression of Nipbl and related developmental genes in mouse cells (Example 3).

Therefore, one embodiment of the invention is a method of treating a subject that is deficient in NIPBL expression, or deficient in expression of a NIPBL homolog or ortholog, or is determined to have CdLS, by administering Indomethacin or Acemetacin in an effective amount, wherein the expression of NIPBL, or the NIPBL homolog or ortholog, in the cells of that subject is increased. Where the subject is a mammal, NIPBL expression levels may be easily determined by examining blood cells for NIPBL mRNA.

In another embodiment of the invention is a method of treating a subject that is deficient in NIPBL expression or deficient in expression of a NIPBL homolog or ortholog, or is determined to have CdLS, by administering Indomethacin or Acemetacin in an effective amount, for an effective period of time, wherein symptoms of CdLS are improved.

In another embodiment is a method of screening potentially therapeutic compounds for beneficial effects to a subject with CdLS, by treating a eukaryotic cell, including a human, mouse, *Drosophila*, or yeast cell, which is either wild type, or deficient in NIPBL expression, or deficient in expression of a NIPBL homolog or ortholog, with a potentially therapeutic compound and determining whether that compound possess the ability to increased expression of NIPBL or related homologs or orthologs in the eukaryotic cell.

In yet another embodiment is a method of screening potentially therapeutic compounds for beneficial effects for a subject with CdLS, by treating *Drosophila* with loss-of-function Nipped-B mutations, with a potential therapeutic compound, for an effective treatment period, during the developmental stages of their life cycle, including from hatching of larvae until pupariation, and determining whether that compound possess the ability to produce a more normal phenotypes in adults.

Indomethacin

Indomethacin or Indometacin and related derivatives including Acemetacin, are non-steroidal anti-inflammatory drugs (NSAID) that are best known for their abilities to inhibit cyclooxygenase (COX) enzymes. Indomethacin is also known to directly inhibit the activity of the glyoxylase I enzyme. Acemetacin is a glycolic acid ester of Indomethacin that is metabolized to Indomethacin and produces less gastric distress. Indomethacin and Acemetacin have many applications including treatment of inflammatory pain, Ankylosing Spondylitis, osteoarthritis, Rheumatoid arthritis, and acute gout. Indomethacin is also used to treat premature infants for patent ductus arteriosus, pregnant women to suppress preterm labor, and Bartter syndrome patients to improve their kidney function and growth from a few weeks of age until early adulthood. At this time it is not known which function or functions of Acemetacin and Indomethacin are responsible for the increasing the expression of NIPBL or improving developmental phenotype observed in *Drosophila*. The Inventors anticipate that equivalent compounds which possess all the functions of Acemetacin and Indomethacin will also be effective at improving expression of NIPBL or alleviating symptoms of CdLS.

Effective Amount

An effective amount of Indomethacin or Acemetacin would be that amount that increases expression of NIPBL or expression of a NIPBL homolog or ortholog. This amount may be determined by a skilled practitioner, typically a medical doctor, by administering and monitoring the subject. It is expected that Indomethacin would be administered daily for an effective treatment period. Indomethacin has been shown to up regulate and down regulate genes when included in the water supply of mice (Murali et al., (2012) Journal of Lipid Research 53, 2186-2197). Based on the reported water consumed by mice, (Bachmanov et al., (2002) Behav Genet., 32(6): 435-443), the Inventors calculated the intake of Indomethacin by these mice to be about 2.4 mg/kg/day. This dosage, which was an effective amount for modifying genetic expression in mice, is within the range of effective amounts of Indomethacin currently used in other indications, particular pediatric indications for Rheumatoid Arthritis, Bartter Syndrome, pain, or Gitelman Syndrome. Daily dosages of Indomethacin are known for adult and pediatric subjects for these and other indications, in particular inflammatory arthritis and Bartter syndrome, and it is expected that these dosages may be used as guidelines. Various dosages and treatments regimens are well known including formulations of immediate or extended release. By way of non-limiting example, a preferred adult dosage for immediate release formulations may be about 25 mg orally every 8 to 12 hours which may be increased by 25 or 50 mg increments every week to a maximum daily dose of about 150 to about 200 mg. By way of example, an extended release formulation may be given 75 mg orally once a day which may be increased to 75 mg orally twice a day. Indomethacin may also be given rectally by way of example at 50 mg every 8 to 12 hours. Pediatric dosages include, by way of non-limiting example for subjects of few weeks old to 20 years of age, 2 mg/kg/day given orally in divided doses which may be titrated upward to a maximum of 4 mg/kg/day or 200 mg per day. Subjects younger than 2 years or older than 14 years of age may also be treated with these dosages. It is preferable that Indomethacin be given with food, immediately after meals, or with antacids, or prostaglandin analogs to reduce gastric irritation. Indomethacin may also be given intravenously. Non limiting examples of intravenously dosages for adult and pediatric usage include less than 0.1 mg/kg to 0.1 mg/kg, preferably about 0.1 mg/kg to about 0.25 mg/kg, or greater than 0.25 mg/kg given once or in serial treatments, daily, or multiple times per day.

An effective amount may also be determined by the amount that increases expression or function of NIPBL or expression of a NIPBL homolog or ortholog in that particular subject.

Analysis of NIPBL or NIPBL Homolog or Ortholog Expression

Analysis of NIPBL or NIPBL homolog or ortholog expression may be monitored by determining levels of NIPBL or NIPBL homolog or ortholog protein or NIPBL or NIPBL homolog or ortholog mRNA from tissues or cells of a subject, including circulating blood lymphocytes. This may be done in any number of ways known in the art including but not limited to the use of immunochemical techniques to determine NIPBL or NIPBL homolog or ortholog protein levels. This may be done by way of example, using enzyme linked immune assays (ELISA) with commercially available antibodies (Bethyl Laboratories, Inc. Cat No. A301-779A), or antibodies as previously described (Lechner et al., (2005) Biochem Biophys. Res. Commun. 331(4):929-37). Alternatively, or in addition to measuring NIPBL or NIPBL homolog or ortholog protein levels, NIPBL or NIPBL homolog or ortholog mRNA levels may also be measured. By way of example, NIPBL or NIPBL homolog or ortholog mRNA levels may be measured relative to an mRNA control standard in the subject's cells. Non-limiting examples of control standards include GAPDH mRNA (human), Gapdh mRNA (mouse), and RpL32 (*Drosophila*), since these mRNA levels are not affected by Indomethacin or Acemetacin (see Table 1). Levels of mRNA complementary to primers for NIPBL or NIPBL homologs or orthologs may be measured relative to levels of mRNA complementary to primers to control genes to determine NIPBL or NIPBL homolog or ortholog expression. By way of example, a subject's circulating lymphocytes may be collected in a blood sample, and specific oligonucleotide primers used to determine levels of NIPBL mRNA relative to levels of control GAPDH mRNA. An example of an NIPBL and GAPDH primer set used by the Inventors is: NIPBL forward primer: 5'-AAAGCACACCCTGA-CAATAAGGC-3' (SEQ ID NO:1); NIPBL reverse primer: 5'-TCCCTCTTGATTTTCGGAATGAC-3' (SEQ ID NO:2); GAPDH forward primer: 5'-CAAGAAGGTGGTGAAG-CAGGC-3' (SEQ ID NO:3); and GAPDH reverse primer: 5'-CGCTGTTGAAGTCAGAGGAGACC-3' (SEQ ID NO:4). These primers are known by the inventors to be complementary to human mRNAs for NIPBL and to be analogous to those used for *Drosophila* and mouse cells in FIGS. 3 and 4. The Inventors used standard procedures to calibrate primers for quantitative real-time polymerase chain reaction.

It may also be necessary to monitor other parameters such as enzyme levels associated with kidney and liver function to assess adverse effects of Indomethacin and adjust the dosage of Indomethacin accordingly.

Effective Treatment Period

An effective treatment period is the time period wherein the administration of an effective amount of Indomethacin or Acemetacin ameliorates, improves, lessens, or reduces the symptoms of CdLS. By way of example, it is expected that administration of Indomethacin or Acemetacin in humans would be continuously, or daily, for weeks, months, or even years. Since the defect caused by NIPBL and cohesin continues throughout life in subjects with CdLS, it is expected that treatment with Indomethacin may be beneficial to CdLS subjects when administered continuously for extended periods of time, during developmental stages, or throughout the life of the subject, to the extent that the treatment may be tolerated. Since it is believed that Indomethacin and Acemetacin correct defects associated with events that take place during the development and growth of an individual, an effective treatment period would be that required for a significant number of cellular divisions to take place. Also, as was observed in *Drosophila*, an effective treatment period is preferably that

TABLE 1

Examples of primers or that may be used to monitor expression levels of NIPBL or NIPBL homologous or orthologous genes.

| NIPBL homolog or ortholog | Primer | Sequence | Sequence ID Number |
|---|---|---|---|
| human NIPBL | forward primer | 5'-AAAGCACACCCTGACAATAAGGC-3' | (SEQ ID NO: 1) |
| human NIPBL | reverse primer | 5'-TCCCTCTTGATTTTCGGAATGAC-3' | (SEQ ID NO: 2) |
| human GAPDH (control) | forward primer | 5'-CAAGAAGGTGGTGAAGCAGGC-3' | (SEQ ID NO: 3) |
| human GAPDH (control) | reverse primer | 5'-CGCTGTTGAAGTCAGAGGAGACC-3' | (SEQ ID NO: 4) |
| mouse Nipbl | forward primer | 5'-TGAAACCCCAAAGCAAAAGAGTG-3' | (SEQ ID NO: 5) |
| mouse Nipbl | reverse primer | 5'-AGTCTCAGGTCGTCCATCACCC-3' | (SEQ ID NO: 6) |
| mouse Gapdh (control) | forward primer | 5'-GCAAGGACACTGAGCAAGAGAGG-3' | (SEQ ID NO: 7) |
| mouse Gapdh (control) | reverse primer | 5'-TTATTATGGGGGTCTGGGATGG-3' | (SEQ ID NO: 8) |
| *Drosophila* Nipped-B | forward primer | 5'-AGGTTATGCGAGTCGTGGACC-3' | (SEQ ID NO: 9) |
| *Drosophila* Nipped-B | reverse primer | 5'-GCGGTTTAGTAGTGCGAAGAAGTG-3' | (SEQ ID NO: 10) |
| *Drosophila* RpL32 (control) | forward primer | 5'-ATCGGTTACGGATCGAACAAGC-3' | (SEQ ID NO: 11) |
| *Drosophila* RpL32 (control) | reverse primer | 5'-GTTCTGCATGAGCAGGACCTCC-3' | (SEQ ID NO: 12) |

NIPBL protein or mRNA levels may be also compared to historic or pretreatment baseline levels.

which occurs during the developmental stages of life. It is expected that Indomethacin or Acemetacin would have a beneficial effective for the symptoms of CdLS subjects when administered during the developmental stages in humans, by way of example, from a few weeks after birth up to young adulthood, similar to the method used to treat Bartter syndrome. Preferably, treatment with Indomethacin or Acemetacin would be administered during those years most critical to development, for example, from just before or after birth to: 2 years, 4 years, 8 years, 12 years, 16 years, or 20 years of age. Although it is desirable to start Indomethacin or Acemetacin treatment as early as possible, it is realized that the subject may not be diagnosed just before or after birth. Therefore treatment would preferably begin as soon as practical after a diagnosis of CdLS. In addition, since it is known that the brain remains plastic through life it is also expected that adults may be treated with Indomethacin or Acemetacin to improve cognitive function.

Symptoms of CdLS, by way of example, growth (weight and size), cognitive function, behavior, autism rating, cardiac, gut and kidney structural abnormalities, and blood platelet counts may be monitored, by the skilled artisan, typically a medical doctor and dosages or effective treatment period adjusted accordingly. This may be done by monitoring improvements in physical development or cognitive function compared to historic controls (Kline et al., (2007) Am. J. Med. Genet. A 143A(12):1287-96; Nakanishi et al., (2012) Am. J. Med. Genet. A 158A(8):1841-7) or medical history of the individual.

Methods of Screening Potential Therapeutic Compounds for Beneficial Effects to Subjects with Cornelia de Lange Syndrome The Inventors also disclose methods of screening potential therapeutic compounds for beneficial effects to subjects with CdLS. The methods comprise, treating a eukaryotic cell, by way of example a human, mouse, Drosophila, or yeast cell, which is either wild type, or deficient in NIPBL expression or expression of a NIPBL homolog or ortholog, with a potentially therapeutic compound, and determining whether that compound possess the ability to increase the expression of NIPBL or NIPBL homologs or orthologs.

In one example, the eukaryotic cells may be mutant yeast cells, by way of examples yeast scc2 and mis4 mutants. Potential therapeutic compounds may be included in the culture media of yeast scc2 and/or yeast mis4 mutants and any number of methods know in the art may be used to determine whether the potential therapeutic compounds have the ability to improve the growth rate of these mutant yeast (see Example 1). One example of a method of measuring the growth rate of yeast in culture includes monitoring the optical density of the culture medium.

In another example, eukaryotic cells, for example Drosophila ML-DmBG3 cells or mouse C2C12 myogenic cells, or human cells derived from a subject suffering from CdLS, may be maintained in culture, and a potential therapeutic compound added to the culture media. An example of a human cell derived from a subject suffering from CdLS may be a fibroblast (see Vrouwe et al., (2007) Human Molecular Genetics; 16:12, 1478-1487). Any number of methods known in the art may be used to determine whether the potential therapeutic compound possess the ability to increase expression of NIPBL or a NIPBL homolog or ortholog. Examples of methods of determining the expression of NIPBL or a NIPBL homolog or ortholog include measuring levels of NIPBL or NIPBL homolog or ortholog protein levels or measuring NIPBL or NIPBL homolog or ortholog mRNA levels as described above.

In yet another example, potential therapeutic compounds may be included to the culture media of Drosophila larvae with reduced expression of Nipped-B. In one example, Drosophila larvae with Nipped-B mutation concurrent with an $N^{spl-1}$ mutation may be used to test potential therapeutic compounds. The $N^{spl-1}$ mutation, when concurrent with the Nipped-B mutation is dominantly suppressed, resulting in a more normal appearing eye (see Rollins et a al., (1999) Genetics; 152 (2):577-93). Treatment with Acemetacin elevates Nipped-B gene expression and enhances the $N^{spl-1}$ phenotype, decreasing the size of the eye. Potential therapeutic compounds may be assayed for their ability to elevate expression of the Nipped-B gene which will enhance the $N^{spl-1}$ phenotype, resulting in a decrease in the size of the eye relative to similar untreated subjects.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLES

Methods and Materials

Indomethacin and Acemetacin were purchased from Sigma Chemical Company, dissolved in DMSO or phosphate-buffered saline (PBS) and applied by dilution into yeast cultures, Drosophila food, or culture media of Drosophila and mouse cells at various concentrations up to 600 micromolar. Controls for drug treatment in all examples was the equivalent amount of vehicle (DMSO or PBS) used to deliver the drug. Wild-type and mutant yeasts were grown at temperatures that limited their growth and growth was scored by optical density over time to measure both growth rate and growth maxima. Drosophila mutant phenotypes were scored quantitatively with regard to wing, eye, and bristle development after treatment after they were grown in drug-containing food from hatching of larva until pupariation (approximately 5 days). Drosophila ML-DmBG3 cells were treated with various concentrations of Indomethacin and Acemetacin for 1 to 3 days in Schneider's media containing 10% fetal calf serum and 10 micrograms per milliliter insulin at 25° C. RNA was extracted and analyzed to determine RNA levels for various genes (Nipped-B, Rad21, E(spl)-C, invected, engrailed, etc.) with RpL32 transcripts as the standard using quantitative real-time reverse transcription PCR by methods similar to those described in Schaaf et al. (2009). PLoS One; 4(7):e6202, herein incorporated by reference. Mouse C2C12 cells were cultured under subconfluent conditions in Dulbecco's Modified Eagles Medium (DMEM) containing 10% fetal calf serum at 37° C. with pH control, and treated with various concentrations of Indomethacin for up to three days before extraction of RNA and measurement of RNA levels for Nipbl, Rad21, Cebpa, Pparg, Myod1, and Myog by RT-PCR with Gapdh RNA as the standard.

Example 1

The Inventors began their screening with a library of FDA-approved drugs for their ability to improve the growth of yeast strains with temperature-sensitive mutations in the NIPBL homologs or orthologs. These included the scc2-4 (Nipped-B) mutation, the smc3-42 (cohesin) mutation, mcd1-1 (cohesin) and pds5-1 (Pds5 cohesion maintenance factor) mutation in Saccharomyces cerevisiae, and the mis4-242 (Nipped- B) mutation, and rad21-K1 (cohesin) mutation in *Schizosaccharomyces pombe*. These mutant strains and their parental strains were grown at semipermissive temperatures that partially inhibited growth, and a library of FDA-approved drugs purchased from Sigma Chemical Company was screened for compounds that selectively improved the growth rate of the mutant strains, as measured by both growth rate and maximal growth (data not shown). Compounds that improved the growth rate and/or growth maxima of one or more of the mutant strains relative to the parental strains were retested. An improvement in growth rate was defined as a reproducible increase in either the rate of cell division of a mutant yeast strain during the logarithmic growth or the maximal culture density or both as determined by taking the optical density of the culture every 30 min relative to a vehicle control, and the wild-type yeast controls. Only a few compounds were identified that improved the growth of the mutant strains. The most well tolerated and therefore the most promising for long term administration were Indomethacin and the Acemetacin derivative of Indomethacin, which are both non-steroidal anti-inflammatory (NSAID) compounds. Indomethacin is used in premature infants for the purpose of treating patent ductus arteriosus, in pregnant mothers to suppress pre-term labor, and Bartter syndrome patients from a few weeks of age until early adulthood, and thus is considered safe for the predicted patient population. For this reason, Indomethacin and Acemetacin were chosen for further evaluation.

Example 2

Figure 2:
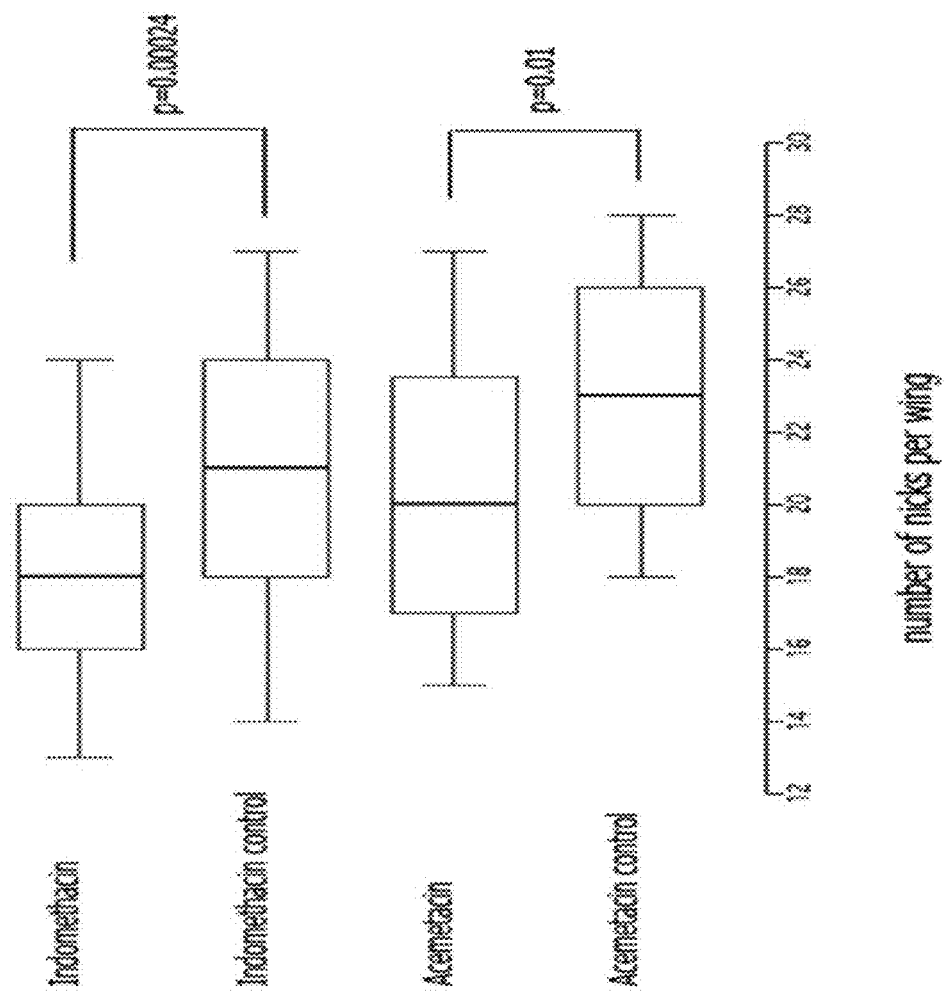
FIG. 2 shows a decrease in the adult wing margin-nicking mutant phenotype of the $cut^K$ mutation by feeding Indomethacin and Acemetacin to Drosophila larva from the time of hatching until pupariation. Controls were feed the solvent that was used to dissolve the compounds (DMSO for Indomethacin, PBS for Acemetacin).

The Inventors tested the effects of Indomethacin and Acemetacin on mutant phenotypes in *Drosophila* that are sensitive to Nipped-B gene dosage. The $ct^K$ mutation in the cut gene causes a wing-nicking defect is strongly enhanced by heterozygous Nipped-B mutations. The inclusion of Indomethacin or Acemetacin in the food source from the early larval stages of development has the effect of reducing the occurrence of this developmental defect, which is observed as the wing nicking (FIG. 2).

The $N^{spl-1}$ mutation in the Notch receptor gene causes a small rough eye phenotype. This mutation, when concurrent with Nipped-B mutations is dominantly suppressed, and reducing Nipped-B gene expression increases eye size in $N^{spl-1}$. (Rollins et a al., (1999) Genetics; 152 (2):577-93). Treatment with Acemetacin enhances the $N^{spl-1}$ phenotype, decreasing the size of the eye, as would be expected if expression of the Nipped-B gene is elevated (data not shown).

Figure 3:
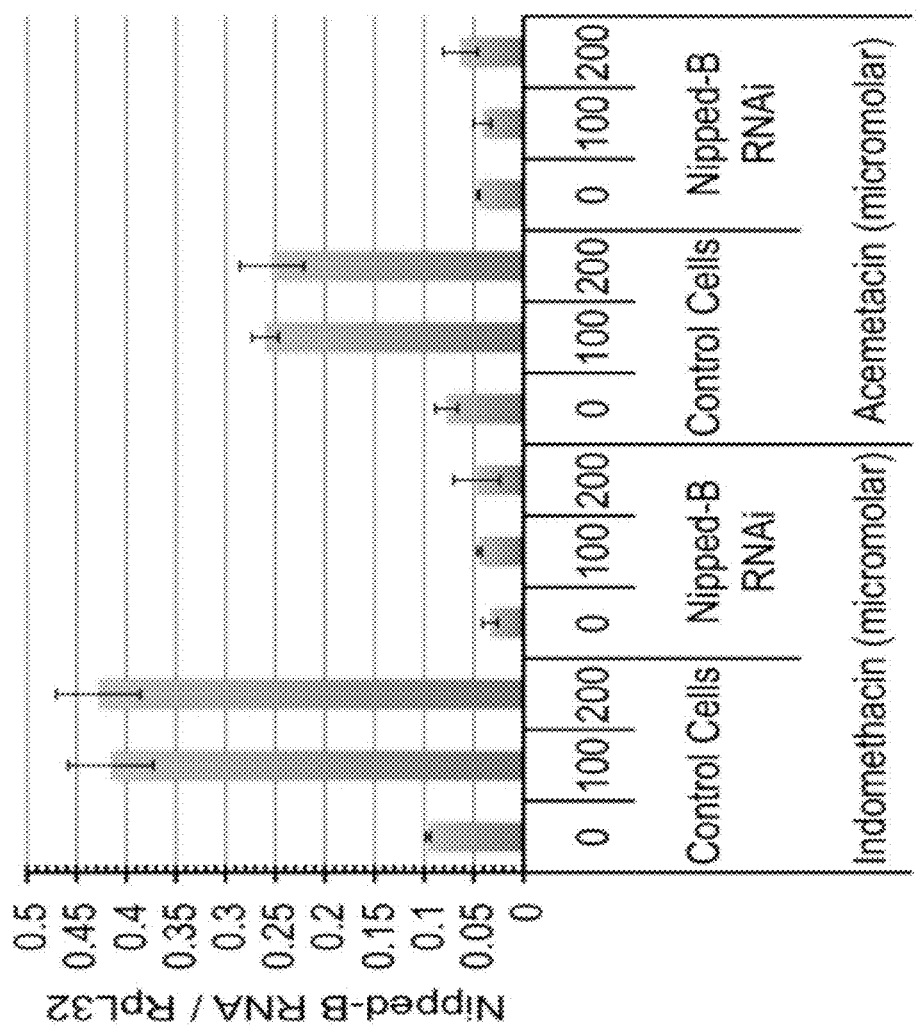
FIG. 3 shows that Indomethacin and Acemetacin treatment for 48 hours increases Nipped-B mRNA levels in Drosophila cultured BG3 cells derived from the brain. Nipped-B RNAi cells are treated with double-stranded RNA to destabilize Nipped-B RNA, and suppress the effect of Indomethacin.

Indomethacin and Acemetacin increase Nipped-B gene RNA transcripts in cultured *Drosophila* cells (ML-DmBG3) derived from larval brain (FIG. 3). The effect is also blocked by Nipped-B RNAi (FIG. 3). Indomethacin and Acemetacin reduce the effect of cohesin depletion on expression on other genes (not shown). At very high levels, both Indomethacin and Acemetacin have some toxicity, and the effect on Nipped-B RNA levels is reduced.

Example 3

Figure 4A:
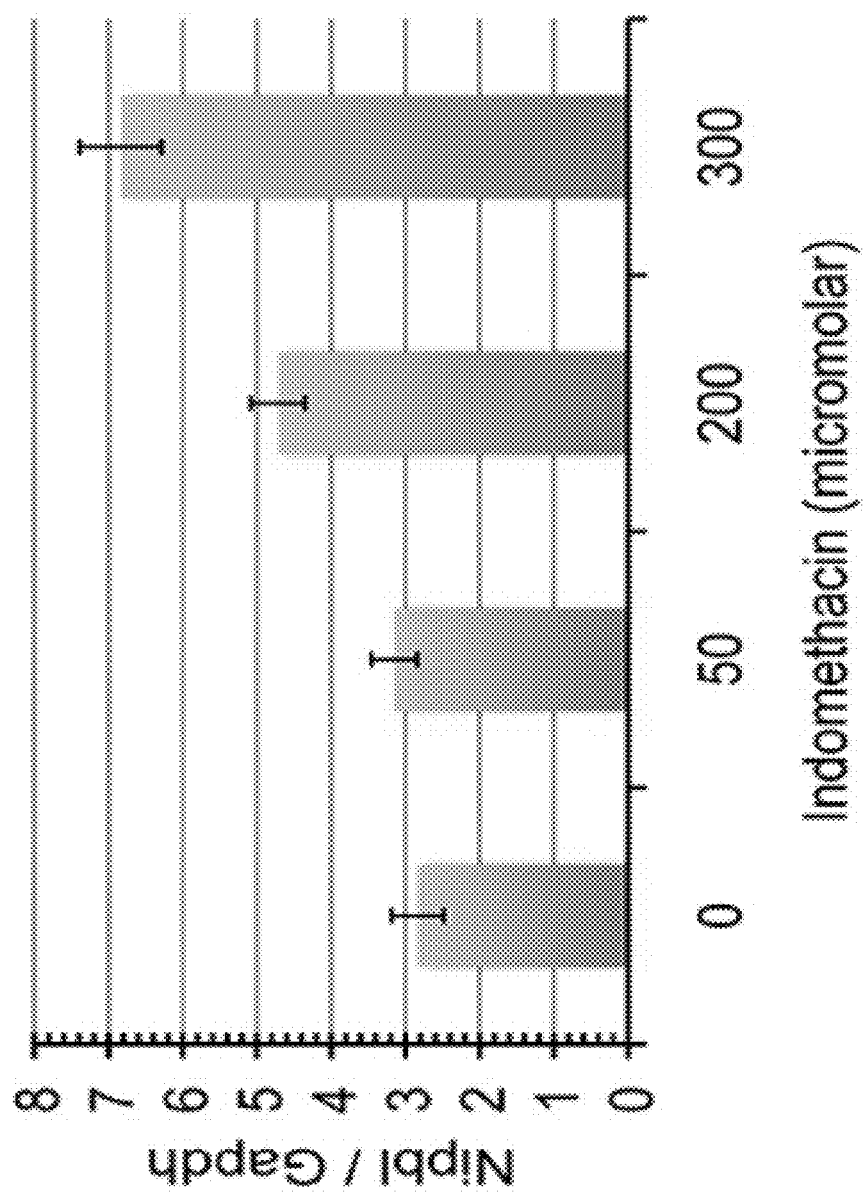
FIG. 4A shows that Indomethacin increases Nipbl mRNA in mouse C2C12 myogenic cells.
Figure 4B:
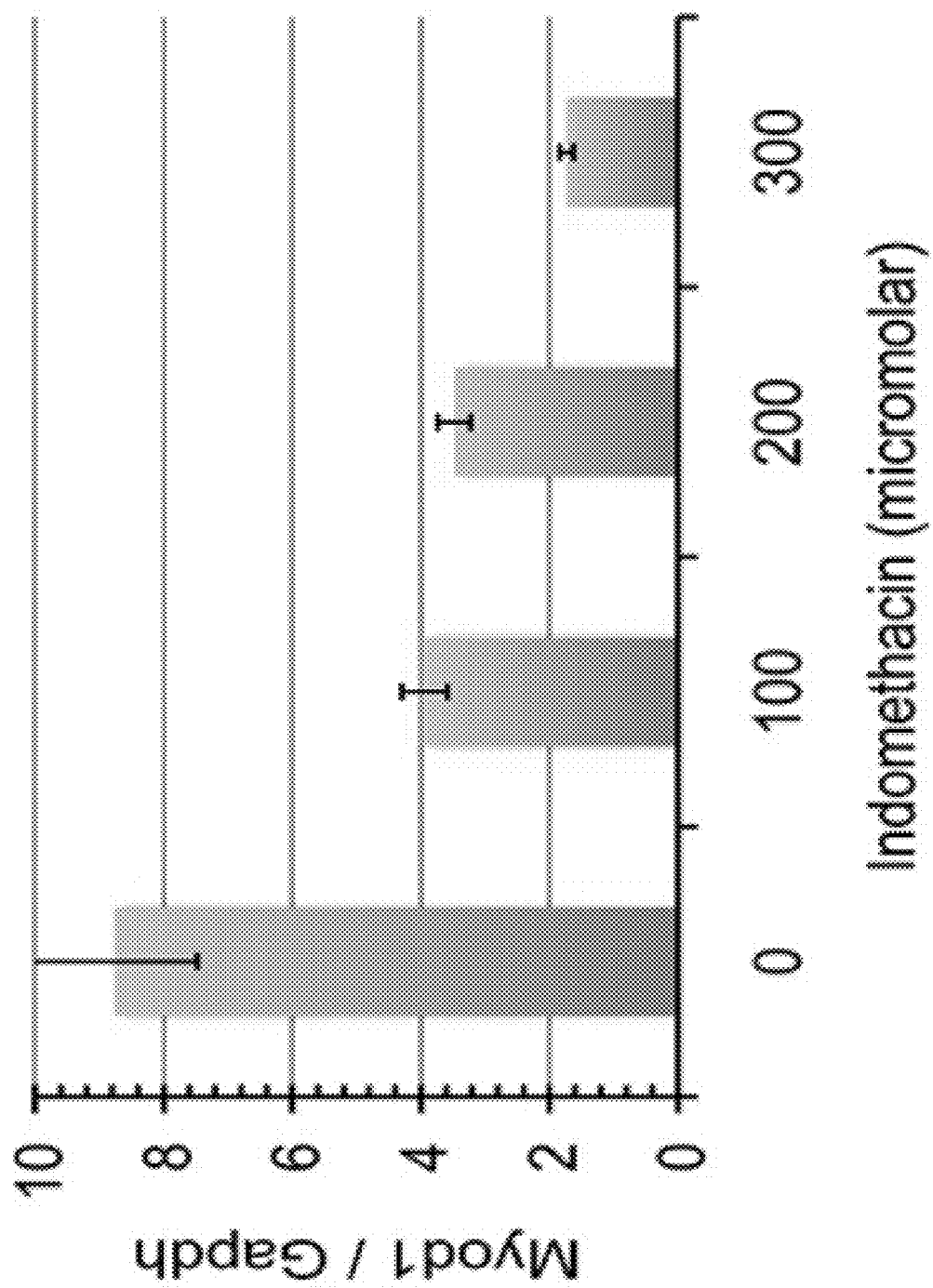
FIG. 4B shows that Indomethacin decreases the expression of Myod1 in mouse C2C12 myogenic cells after treatment for 3 days.
Figure 4C:
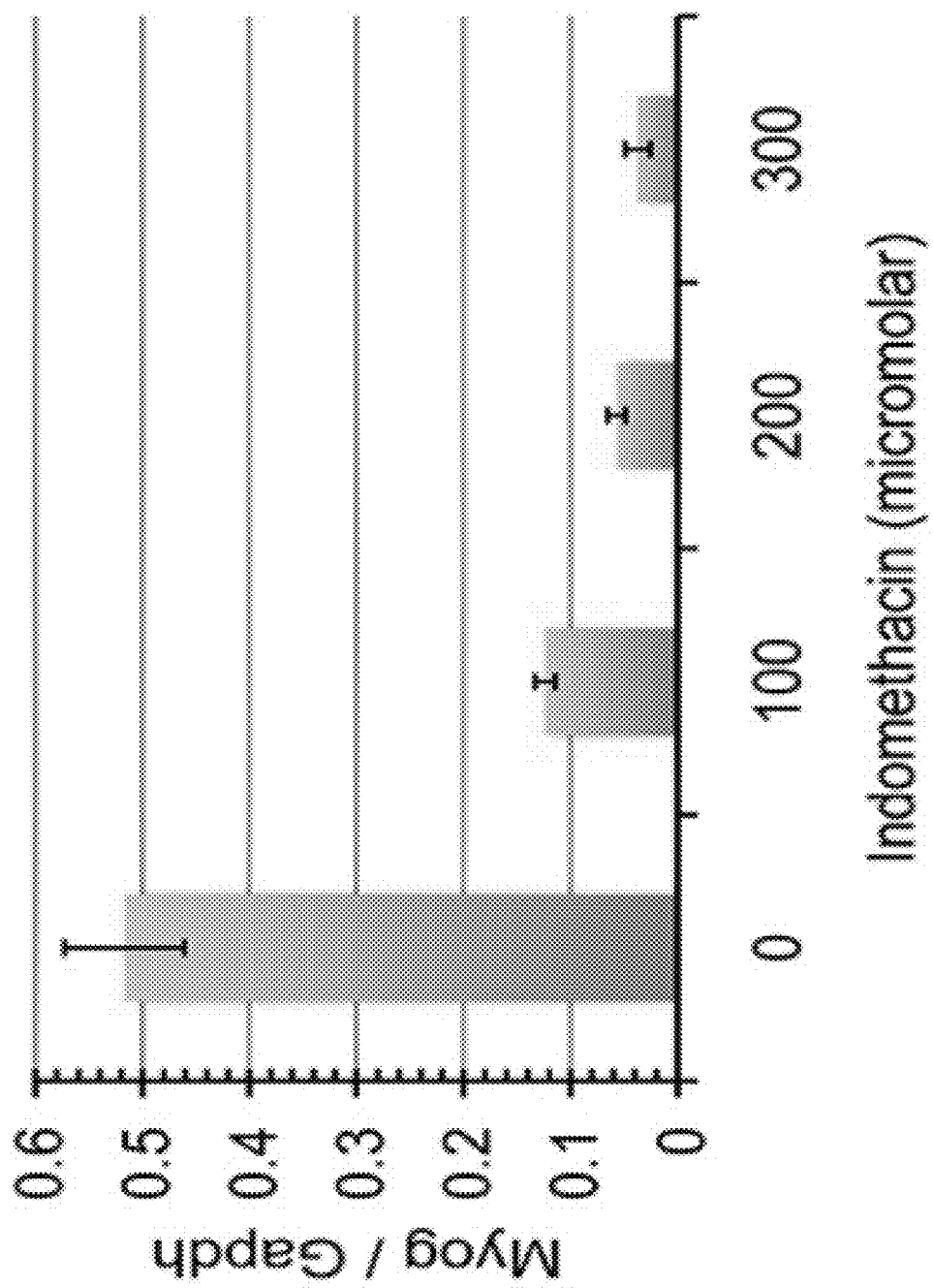
FIG. 4C shows that Indomethacin decreases the expression of Myog myogenic genes, in mouse C2C12 myogenic cells after treatment for 3 days.
Figure 4D:
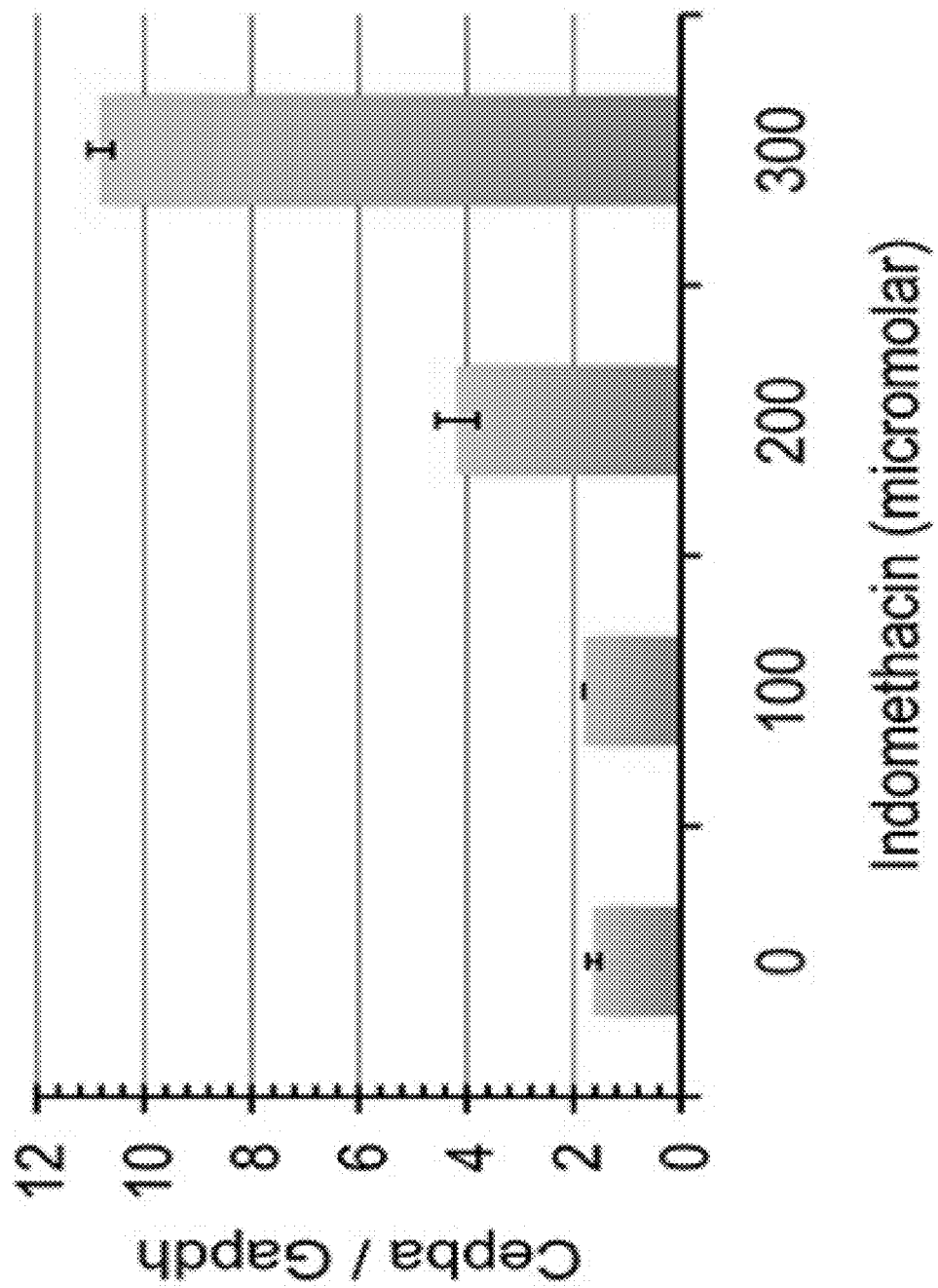
FIG. 4D shows that Indomethacin increases expression of the Cepba adipogenic genes in mouse C2C12 myogenic cells after treatment for 3 days.
Figure 4E:
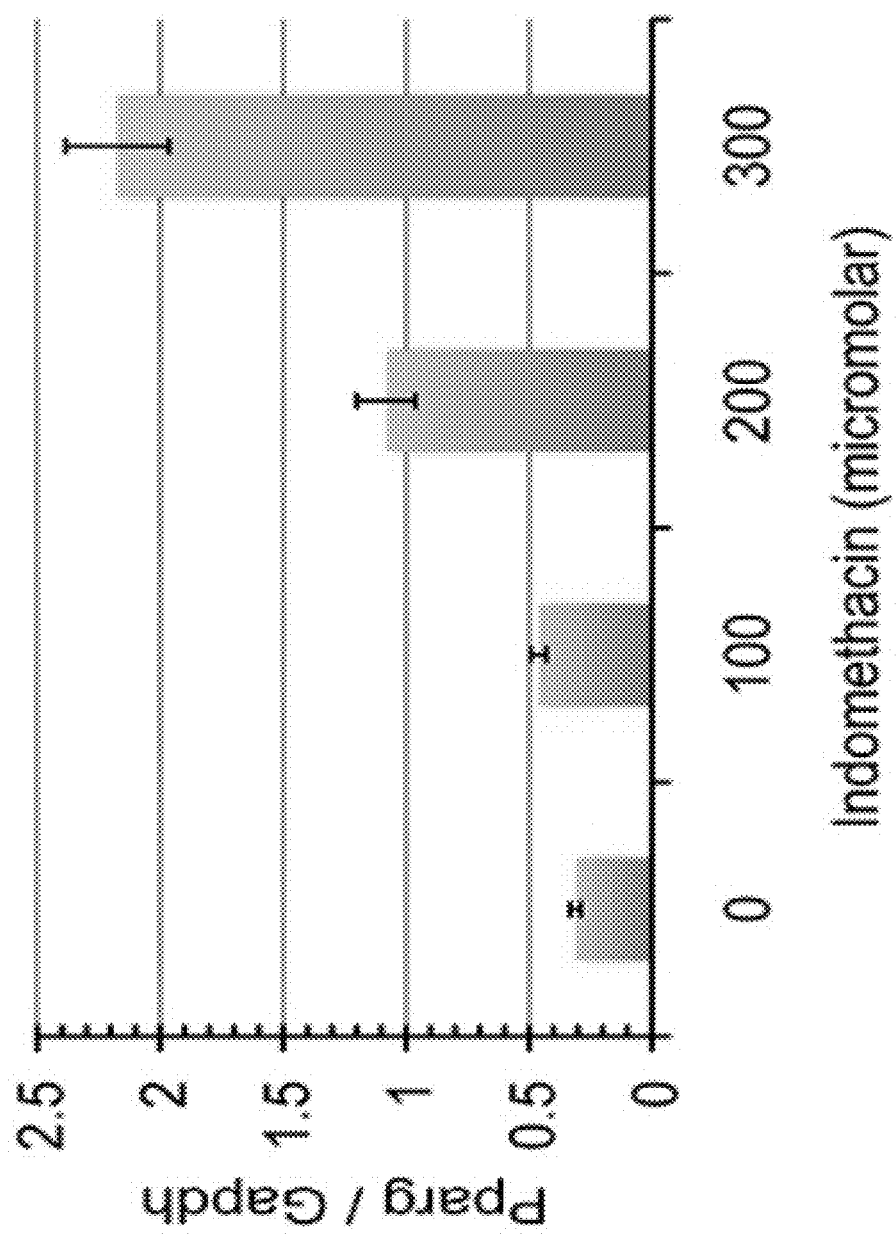
FIG. 4E shows that Indomethacin increases expression of Pparg adipogenic genes in mouse C2C12 myogenic cells after treatment for 3 days.

Indomethacin also increases expression of Nipbl in mouse C2C12 myogenic cells (FIG. 4A). In addition, Indomethacin also reduced expression of the Myod1 (FIG. 4B) and Myog (FIG. 4C) myogenic genes, and increased expression of the Cepba (FIG. 4D) and Pparg (FIG. 4E) adipogenic genes. Expression of these and other adipogenic genes is reduced in Nipbl +/− mice (Kawauchi et al. (2009) PLoS Genet.; 5(9): e1000650), which may explain their reduced fat levels, and potentially why individuals with CdLS tend to be lean.

CdLS individuals usually have a lean body habitus, and in the mouse CdLS model, there is a deficiency in adipogenesis, attributed to reduced expression of transcription factors, including C/EBPβ. Id. Indomethacin promotes adipogenesis in mesenchymal stem cells by increasing expression of C/EBPβ and PPARγ2 independently of COX inhibition (Styner et al., (2010) J Cell Biochem. 1; 111 (4):1042-50).

All publications and patents cited in this specification are hereby incorporated by reference in their entirety. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating Cornelia de Lange Syndrome (CdLS) in a subject comprising, administering an effective amount of Indomethacin or Acemetacin to the subject, wherein cellular expression levels of NIPBL or NIPBL homologous or orthologous mRNA are increased.

2. The method of claim 1, wherein the subject is a human and expression levels of NIPBL mRNA are measured in blood cells.

3. The method of claim 1 wherein the subject is an adult human and the effective amount is about 150 mg to about 200 mg administered orally per day.

4. The method of claim 1 wherein the subject is a pediatric human and the effective amount is a daily dose of 2 to 4 mg administered orally.

5. The method of claim 1 wherein the subject is a human, and the effective amount is an intravenous dose from about 0.1 mg/kg to about 0.25 mg/kg, per day.

6. The method of claim 1 wherein, the effective amount of Indomethacin or Acemetacin is administered, for an effective treatment period, wherein the symptoms of CdLS are improved.

7. The method of claim 6 wherein the effective treatment period comprises a juvenile period for the subject.

8. The method of claim 6 wherein the subject is a human and the effective treatment period begins before or just after birth.

9. The method of claim 6 wherein the subject is a human and the effective treatment period begins just after a diagnosis of CdLS.

10. The method of claim 6 wherein the subject is a human and the effective treatment period comprises a period of time from a few weeks after birth until 20 years of age.

11. The method of claim 6 wherein the subject is a human and the effective treatment period comprises a period of time from a few weeks after birth until 10 years of age.

12. The method of claim 6 wherein the subject is a human and the effective treatment period comprises a period of time from a few weeks of age until 5 years of age.

13. The method of claim 6 wherein the subject is a human and the effective treatment period comprises a period of time from a few weeks of age until 2 years of age.

14. The method of claim 6 wherein symptoms are selected from the group consisting of reduced growth, behavior, autism rating, cardiac abnormalities, gut abnormalities, kidney structural abnormalities, blood platelet counts, and reduced cognitive function.

15. The method of claim 1 wherein the subject is a mammal and the effective amount is a daily dose of about 2.4 mg administered orally.

16. The method of claim 1 wherein the subject is an adult human and the effective amount is a daily dose of about 25 mg every 8 to 12 hours administered orally.

17. The method of claim 16 wherein the effective amount is increased by 25 mg or 50 mg increments every week to a maximum daily dose of about 150 to about 200 mg.

18. The method of claim 1 wherein the subject is a pediatric human and the effective amount is a daily dose of about 50 mg every 8 to 12 hours given rectally.

19. A method of treating Cornelia de Lange Syndrome (CdLS) in a subject comprising, administering an effective amount of Indomethacin or Acemetacin to the subject, for an effective treatment period, wherein cellular expression levels of NIPBL or NIPBL homologous or orthologous mRNA are increased.

20. The method of claim 19 wherein, the effective treatment period consists of a period comprising a few weeks after birth up to young adulthood of the subject, and wherein the symptoms of CdLS are improved.

* * * * *